United States Patent [19]
Schmidt

[11] Patent Number: 6,028,694
[45] Date of Patent: Feb. 22, 2000

[54] ILLUMINATION DEVICE USING PULSE WIDTH MODULATION OF A LED

[76] Inventor: Gregory W. Schmidt, 2724 El Camino del Norte, Olivenhain, Calif. 92024

[21] Appl. No.: 09/083,572

[22] Filed: May 22, 1998

Related U.S. Application Data

[60] Provisional application No. 60/047,445, May 22, 1997.

[51] Int. Cl.[7] ...................................................... G02F 1/03
[52] U.S. Cl. .......................... 359/264; 362/119; 362/109; 345/60; 349/25; 315/246
[58] Field of Search ........................... 359/264; 362/119, 362/109, 231, 294; 345/60, 95; 349/25, 37; 315/246

[56] References Cited

U.S. PATENT DOCUMENTS

| | | | |
|---|---|---|---|
| 4,268,750 | 5/1981 | Cowart | 250/315.1 |
| 4,887,074 | 12/1989 | Simon et al. | 340/782 |
| 4,897,639 | 1/1990 | Kanayama | 340/812 |
| 5,043,634 | 8/1991 | Rothwell, Jr. et al. | 315/246 |
| 5,127,405 | 7/1992 | Alcala et al. | 128/633 |
| 5,311,351 | 5/1994 | Chesnoy | 359/264 |
| 5,334,855 | 8/1994 | Moyer et al. | 257/13 |
| 5,436,742 | 7/1995 | Tanaka et al. | 359/56 |
| 5,519,496 | 5/1996 | Borgert et al. | 356/394 |
| 5,589,852 | 12/1996 | Thompson et al. | 345/147 |
| 5,596,671 | 1/1997 | Rockwell, III | 385/147 |
| 5,614,961 | 3/1997 | Gibeau et al. | 348/750 |
| 5,629,716 | 5/1997 | Okamoto et al. | 345/60 |
| 5,634,711 | 6/1997 | Kennedy et al. | 362/119 |

*Primary Examiner*—Loha Ben
*Attorney, Agent, or Firm*—Fish & Richardson P.C.

[57] ABSTRACT

An illumination device utilizing a pulse modulation technique of a solid state light source to provide increased light output for a given heat load. In a preferred embodiment, power is supplied in pulses to periodically activate a short wavelength (i.e., blue) emitting LED, which in turn stimulates a phosphor-based color conversion system to produce sustained white light. In response to a pulse of power, the LED emits an intense burst of short wavelength light. The burst of light from the LED briefly excites the phosphor system, producing a bright illumination. During the interval while power is dissipated in the LED, the LED warms. After the pulse ends and before the next pulse begins, the LED cools because no more power is dissipated in the LED. However, the phosphorescent behavior of the phosphor system causes it to continue to glow for a period of time after being excited. The intensity of the illumination produced by the phosphor gradually decays during this period. The average illumination produced by the preferred embodiment over the entire period from the beginning of one pulse to the beginning of the next is higher than a conventional LED illumination device using constant power dissipation for a given heat load.

18 Claims, 7 Drawing Sheets

ILLUMINATION DEVICE USING PULSE WIDTH MODULATION OF A LED

This application claims the benefit of the U.S. Provisional Application No. 60/047,445 filed on May 22, 1997, the entirety of which is incorporated herein by reference.

TECHNICAL FIELD

This invention relates to illumination devices, and more particularly to an illumination device which uses pulse width modulation of an excitatory light emitting diode ("LED").

BACKGROUND

The need in surgery and other areas to illuminate internal and hard to reach areas has long been recognized. Thomas Edison first used a miniature incandescent electric lamp to replace the wax candle as a source for such illumination. However, heat from such lamps has always posed a problem for surgical usage.

A major breakthrough occurred when fiber optics were used to convey light from a remote source of optical radiation to an area where illumination is needed. However, problems with illumination devices such as fiber bundles remain because of their bulk and lack of flexibility. The large minimum bend radius of fiber optics limits their ease of use. Exceeding the bend radius limit is a typical source of failure. Single fiber systems do not solve this problem and are even more prone to failure than bundles of fibers.

A further problem with conventional illumination sources is that the color temperature of incandescent lamps is so low (2,600–3,000° K) that the reddish cast given off by the light diminishes the visibility of important physiological structures in surgical applications. This color rendering problem was partially solved in devices incorporating Xenon arc lamps as their source. The emission spectrum of Xenon provides a whiter illumination. A further problem with Xenon arc lamps exists, however, since they emit a large fraction of their total energy in the invisible infrared and ultraviolet wavelengths. This invisible waste energy part of the Xenon spectrum (both ultraviolet and infrared) ends up as heat. Excess heat is a serious problem in heat sensitive applications, such as many surgical applications, because of tissue dehydration, cooking, and burning, as well as adding to the heat load in operation rooms, which are typically air-conditioned. An additional disadvantage of Xenon arc lamps is that the power level required is typically too high to use an internal power source such as a battery.

Accordingly, the inventor has determined that it would be desirable to have an illumination device which is miniature, cool operating, and convenient to use, and which provides ergonomically correct lighting of scenes which are viewed directly.

SUMMARY

The invention provides methods and apparatus utilizing a pulse modulation technique of a solid state light source to provide increased light output for a given heat load.

In a preferred embodiment, power is supplied in pulses to periodically activate a short wavelength (i.e., blue) emitting LED, which in turn stimulates a phosphor-based color conversion system to produce sustained white light. In response to a pulse of power, the LED emits an intense burst of short wavelength light. The burst of light from the LED briefly excites the phosphor system, producing a bright illumination. During the interval while power is dissipated in the LED, the LED warms. After the pulse ends and before the next pulse begins, the LED cools because no more power is dissipated in the LED. However, the phosphorescent behavior of the phosphor system causes it to continue to glow for a period of time after being excited. The intensity of the illumination produced by the phosphor gradually decays during this period. The average illumination produced by the preferred embodiment over the entire period from the beginning of one pulse to the beginning of the next is higher than a conventional LED illumination device using constant power dissipation for a given heat load.

In one aspect, the invention includes an illumination device including a solid state light source for producing light; a pulse modulation power control circuit for periodically activating the light source to produce light at a level above the light produced by a sustainable steady-state power level; and a luminescent substance for producing illumination, where the luminescent substance produces illumination in response to light from the light source and further where the luminescent substance continues to produce illumination after the light source has stopped producing light; wherein the average light output of the light source is greater than the average light output obtainable from the light source at the sustainable steady-state power level.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

A preferred embodiment of the invention provides an illumination device which produces an increased light output for a given heat load. The preferred embodiment is described in terms of an illumination device for use in surgical applications, however, alternative applications and appropriate configurations are readily discernible to one of ordinary skill in the art.

Figure 1A:
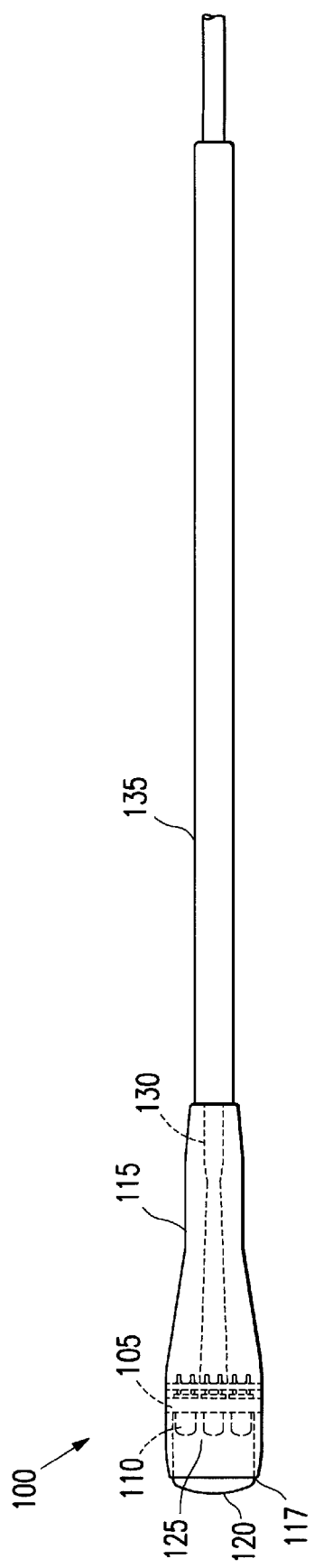
FIG. 1A shows an illumination device according to a preferred embodiment of the present invention.

As shown in FIG. 1A, the preferred embodiment provides an illumination device 100. The illumination device 100 includes a mounting 105, such as a die, upon which is mounted a light source 110. Additional control components may also be included on the mounting 105, described below with reference to FIG. 2. The light source 110 preferably includes at least one solid state light emitting device, such as a light emitting diode ("LED"). The LEDs in the preferred embodiment are preferably short wavelength LEDs. A casing 115 encompasses the mounting 105 and light source 110. The casing 115 includes an opening 117 exposing the light source 110. The casing 115 is preferably made from an opaque and semi-rigid material.

A cover 120 is positioned to cover the opening 117. The cover 120 preferably extends to the mounting 105, such that the light source 110 is enclosed by the mounting 105 and the cover 120. The cover 120 is preferably made from a transparent material. The cover 120 preferably operates as a lens to focus illumination output by the illumination device 100. In an alternative embodiment, the casing 115 and the cover 120 are a single piece of material.

A luminescent substance 125 is placed on the mounting 105. Alternatively, the luminescent substance 125 coats the cover 120 or is interspersed in the material of the cover 120. The luminescent substance 125 is preferably a phosphor, such that the luminescent substance 125 emits light in response to light from the light source 110 and continues to luminesce after the light source ceases to produce light. This delayed light emission is also referred to as "afterglow" or "phosphorescence". The afterglow duration is preferably minimally dependent on temperature, such that the effect of rising temperature on the afterglow duration is minimized. In addition, the luminescent substance 125 preferably emits substantially no heat, and preferably has a characteristic white spectrum. Particularly in medical applications, the luminescent substance preferably contains a minimal amount of biologically hazardous material.

A power connection 130 enters the casing 115 and connects to the mounting 105. The power connection supplies power to the light source 110 from an external power source (not shown). Alternatively, an internal power source, such as a battery, is positioned inside the casing. An internal power source provides improved portability, which is useful in applications such as dentistry. A tube 135 covers the power connection 130 outside the casing 115. In an alternative embodiment, some or all of the additional control components described below with respect to FIG. 2 may be located outside the casing 115 and signals are passed to the illumination device 100 through one or more connections contained in the tube 135. A power control for power activation may be located on the casing 115, the tube 135, or the power source itself. The power control preferably is a switch, such as a screw type on/off switch or a touch or push button. Alternatively, the illumination device 100 may be activated when a cap over the cover 120 is opened. In another embodiment, the power control is a potentiometer or similar variable device that supplies a variable amount of power to the light source 110 to produce a variable level of illumination. The power connection 130 and tube 135 are preferably made from flexible material and at least one of the two is preferably made of a material which retains its shape. Thus, the power connection 130 and tube 135 preferably form a flexible malleable stalk so illumination may be directed to a desired location. One embodiment may have surgical tie-down points to aid in attachment and retention in surgical applications.

The luminescent substance 125 and the light source 110 preferably interact to produce an output illumination which is a white light. The light source 110 preferably emits a short wavelength light (i.e., blue) in response to power applied to the light source 110 through the power connection 130. The luminescent substance 125 in conjunction with the cover 120 produces a sustained white light in response to the light from the light source 110. This white light is the output illumination of the illumination device 100.

Figure 1B:
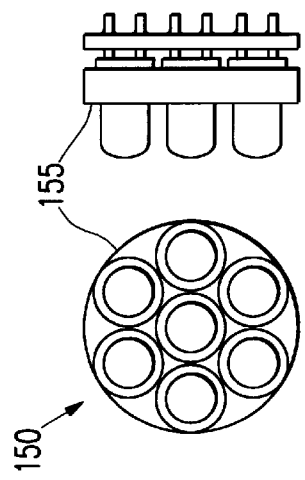
FIG. 1B shows a preferred configuration of LEDs in an illumination device according to a preferred embodiment of the present invention.

FIG. 1B shows a preferred configuration of LEDs 150 on a mounting 155 to be used as the light source 110 and mounting 105 shown in FIG. 1A. Seven LEDs 150 are positioned on a mounting 155 in a regular pattern. Alternatively, configuring the LEDs in two rows driven in parallel, such as one row of three LEDs driven in series and one row of four LEDs driven in series, gives the illumination device a practical shape. Multiple individual LEDs are preferred because they are commonly available. Custom-made LEDs may be used. For example, a single plastic cover may be used over multiple diodes on a circuit die. LEDs may be arranged in a single row if a long narrow light source is appropriate. Numerous alternative configurations are possible depending upon the nature of the application. In addition, all the LEDs may be driven simultaneously or may be driven in some selected order. The mounting 155 is preferably a flat surface or may be curved or of variable curvature to control beam width.

The need for thermal control in the illumination device varies depending upon the application. As described above, surgical applications are typically heat sensitive and require a carefully monitored heat level. In order to maintain a desired heat load (i.e., to prevent the heat emitted by the illumination device from exceeding a certain level), a conductive system such as diamond coatings or copper wires may be used. Alternatively, a convective system such as heat-pipes or Venturi cooling may be implemented. The construction of the thermal control system depends upon the nature of the application. A passive copper wire arrangement is generally preferred as being effective and simple to implement.

Figure 2:
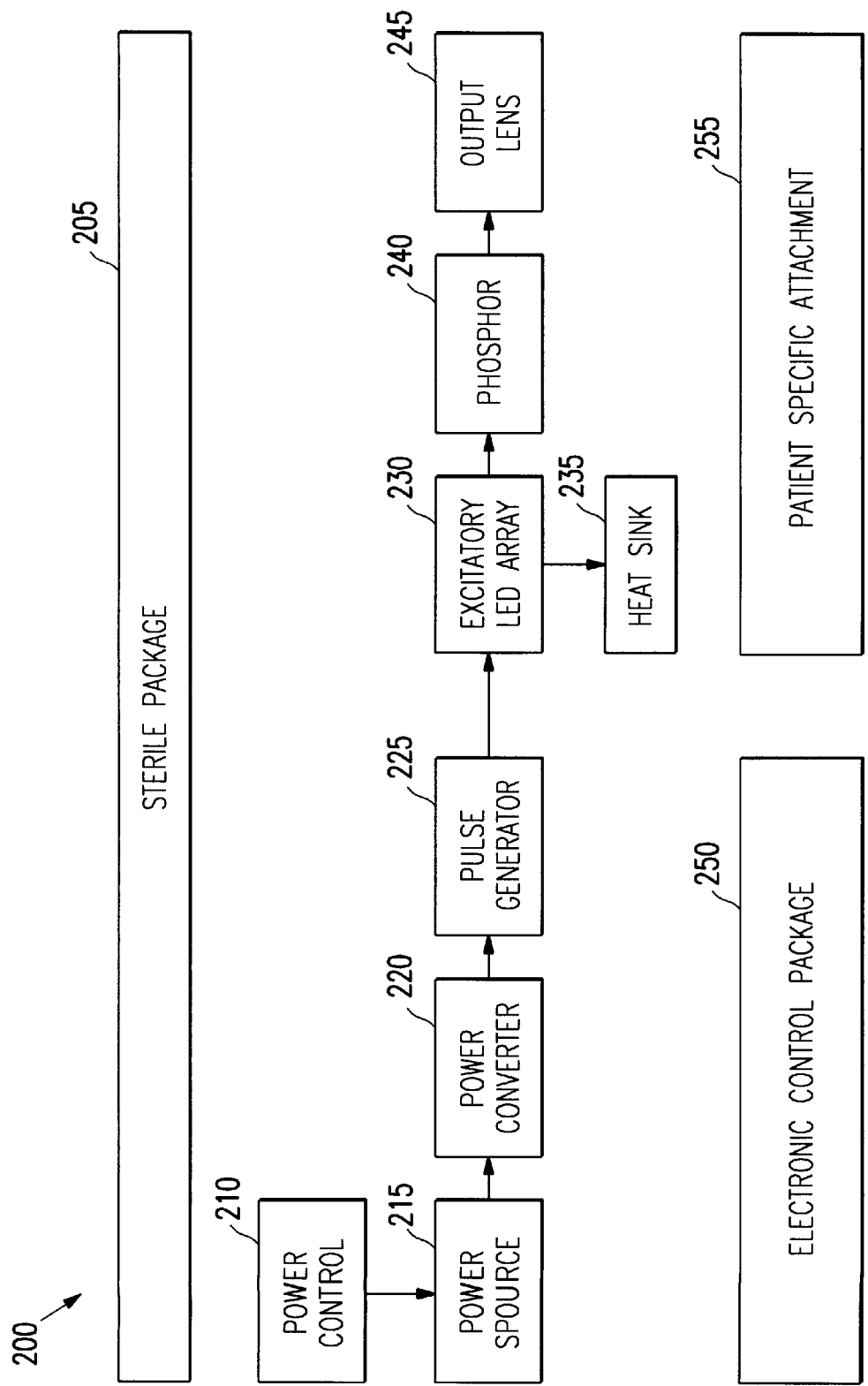
FIG. 2 is a block diagram of components in an illumination device according to a preferred embodiment of the present invention.

FIG. 2 shows a block diagram of components in an illumination device 200 (100 in FIG. 1A) according to the preferred embodiment for a surgical application, including the additional control components noted above. The exterior of the illumination device 200 is formed from a sterile package 205. Attached to the sterile package 205 is a power control 210. The power control 210 is connected to a power source 215. As described above, the power source 215 may be external or internal. The power source 215 supplies power to a power converter 220 in response to the power control 210. The power converter 220 converts the power signal from the power source 215 to a form appropriate to the embodiment and application. The power converter 220 supplies the converted power signal to a pulse generator 225. The pulse generator 225 generates a pulse modulated power signal. The duration and timing of the pulses depend on the nature of the application. Preferably, the duty cycle is approximately 33%, as described in more detail below. The pulse generator 225 supplies the pulse modulated power signal to an excitatory LED array 230 (the light source 110 in FIG. 1A). The excitatory LED array 230 emits light in response to the pulses. Heat generated by the excitatory LED array 230 is at least partially dissipated by a heat sink 235. Light emitted by the excitatory LED array 230 radiates or "pumps" phosphor 240. In response to the light emitted by the excitatory LED array 230, phosphor 240 emits light. The light emitted by phosphor 240 passes through an output lens 245 and is focused as appropriate to be output by the illumination device 200. In addition, an electronic control package 250 supplies control signals to components in the illumination device (connections not shown). The control signals depend on signals received from the components as well as from a patient specific attachment 255 which provides data specific to a patient who is the subject of surgery. Alternative applications may include different configurations of components depending upon requirements such as size, heat, and illumination.

Figure 3:
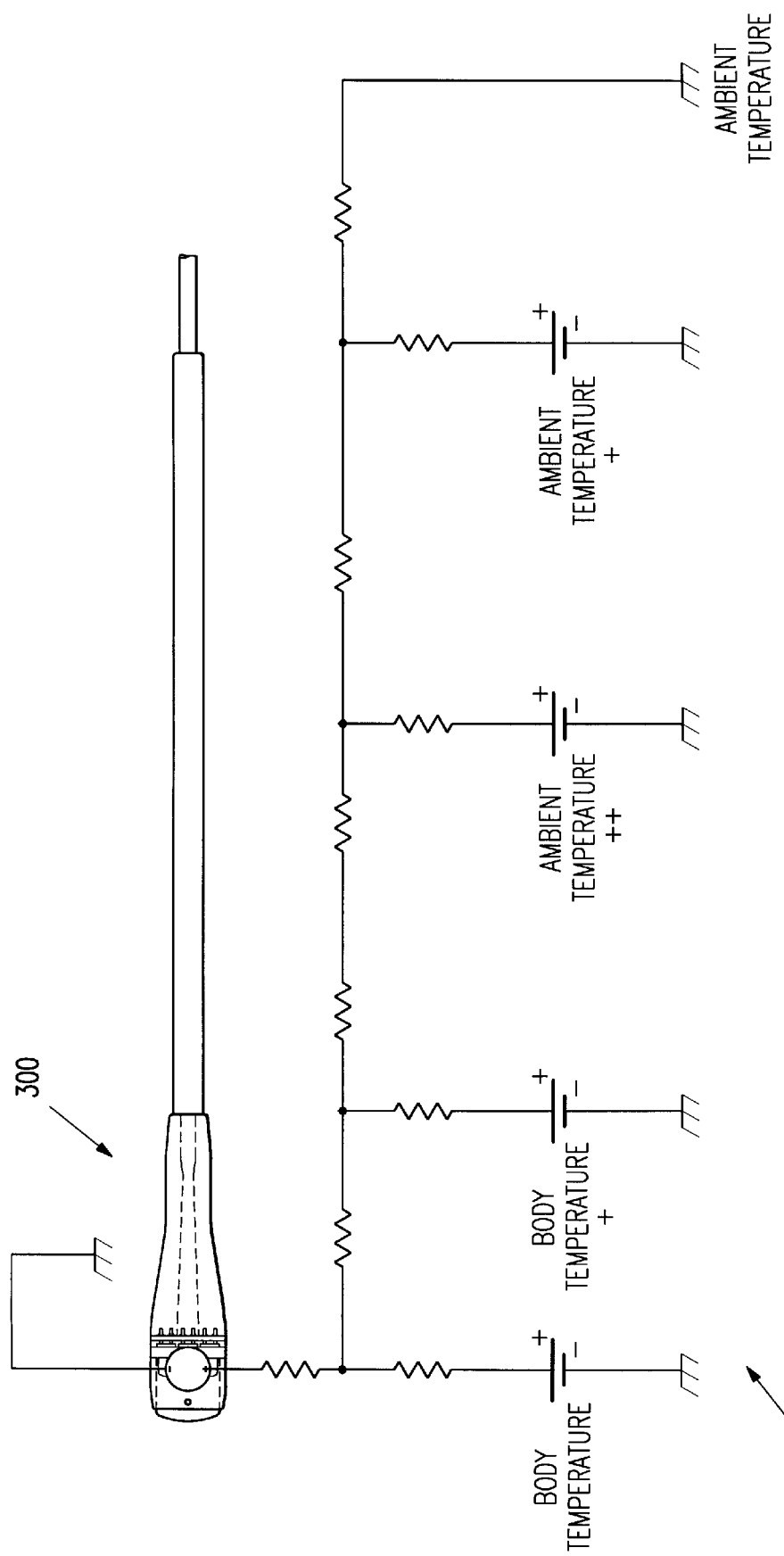
FIG. 3 shows an illumination device connected to a patient specific attachment according to a preferred embodiment of the present invention.

FIG. 3 shows an example of an illumination device 300 (100 in FIG. 1) connected to a patient specific attachment 305 (255 in FIG. 2). The light source of the illumination device 300 operates in response to temperature signals from the ambient environment and the body of a patient. This configuration ensures that the heat emitted by the illumination device 300 does not produce undesirable effects in a surgical application. Similar configurations may be appropriate for alternative applications. For example, an illumination device in a purse preferably does not produce enough heat to damage surrounding material.

Figure 4:
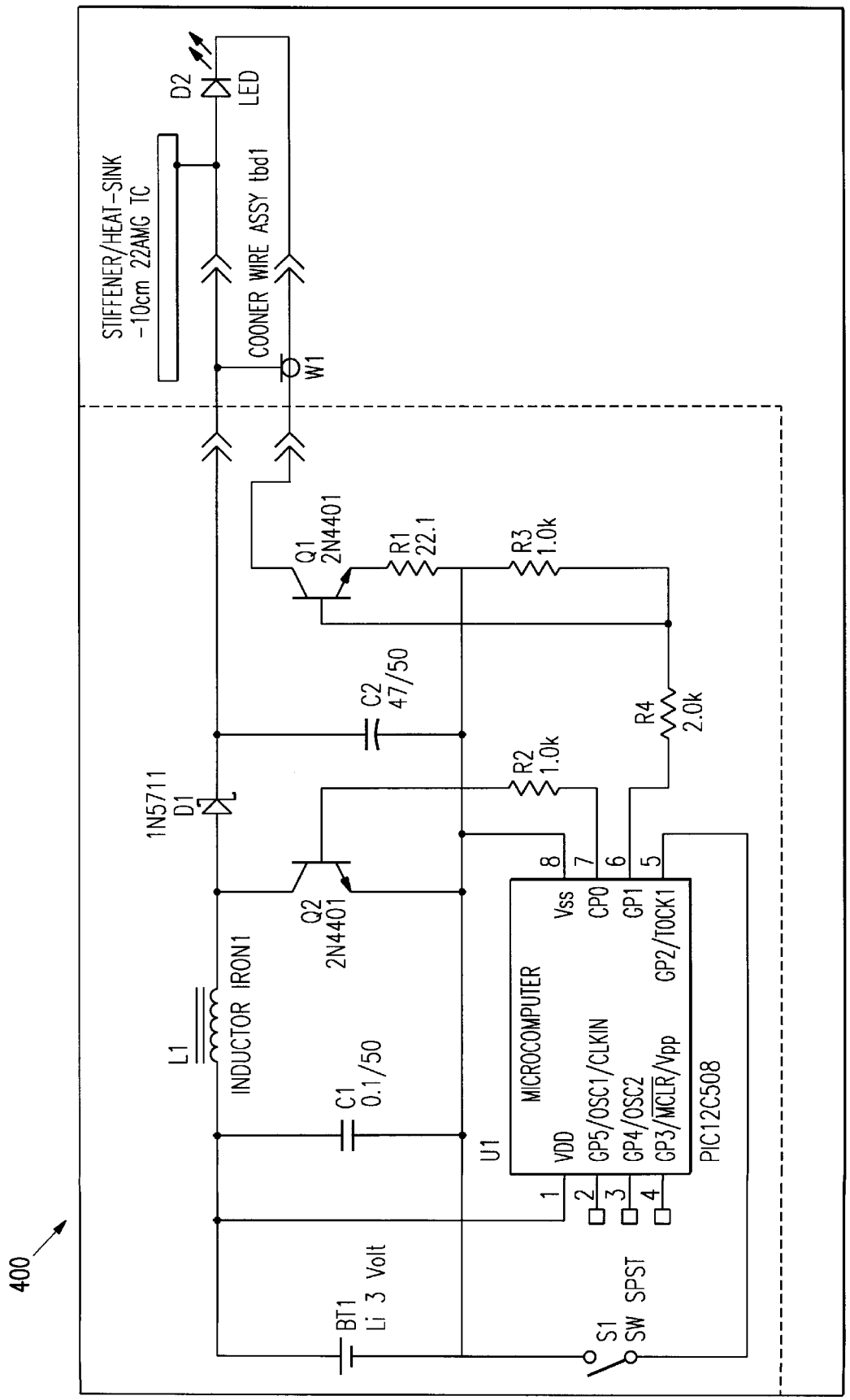
FIG. 4 is a circuit diagram of a preferred circuit configuration for an illumination device according to a preferred embodiment of the present invention.

FIG. 4 is a circuit diagram of an illumination device 400 according to a preferred embodiment. The components shown are a preferred component set, but alternative sets may be used to accomplish a similar function in varying applications.

In operation, the preferred embodiment's light source is driven by a power signal with a pulse waveform. Each pulse activates the light source which emits light and pumps the luminescent substance to produce light at a level above the light produced by a sustainable steady-state (DC) power level. The luminescent substance begins to emit light at the substance's characteristic peak intensity. The light from the luminescent substance is output as illumination of the illumination device. When the pulse is over, the light source ceases to emit light and begins to cool. The luminescent substance continues to emit light after the light source ceases to emit light. The intensity of the light emitted by the luminescent substance decays at a rate characteristic to that substance. Preferably before the luminescent substance has ceased to emit light, the next pulse begins and the light source once again is activated.

Figure 5:
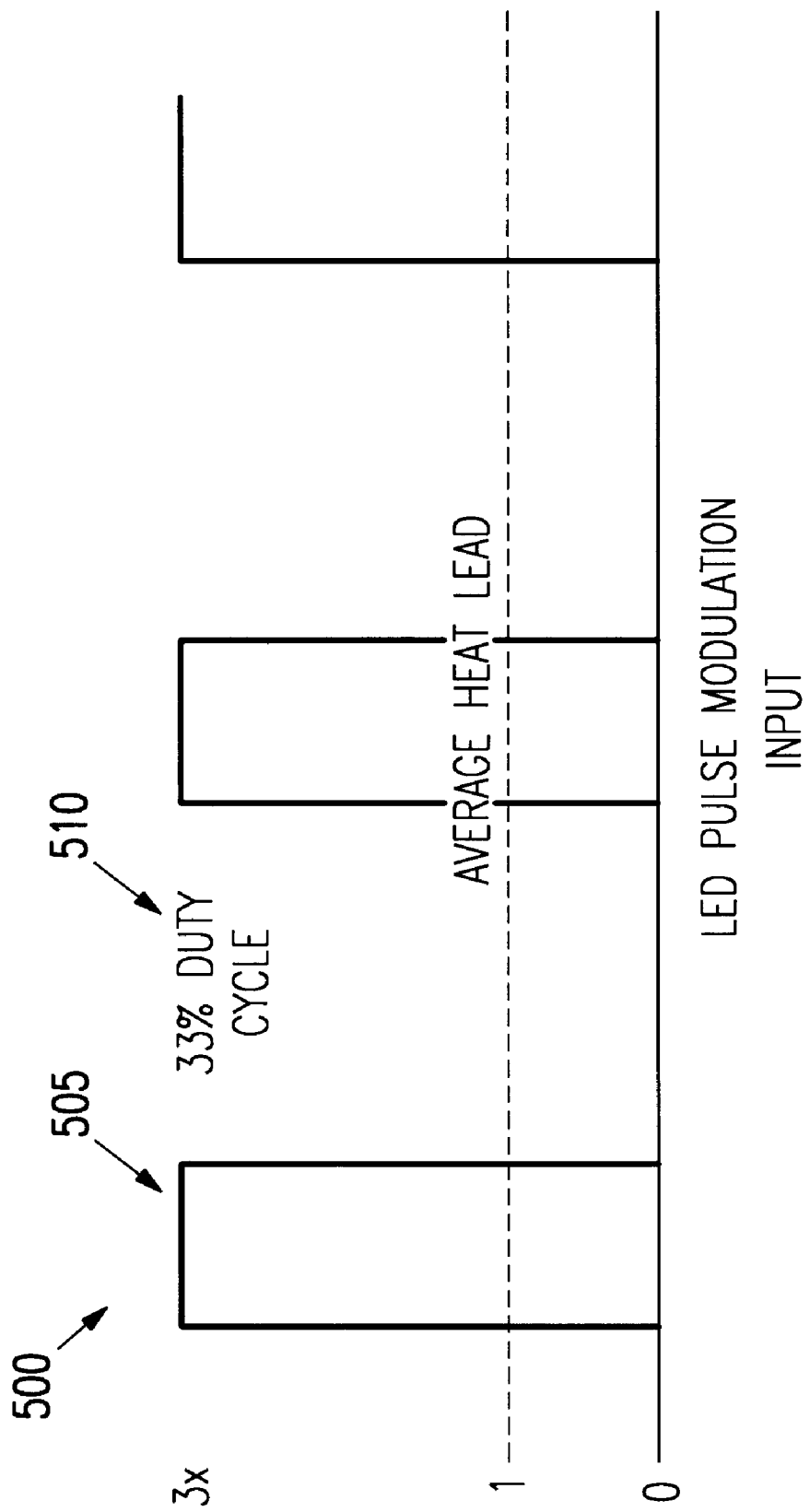
FIG. 5 is a chart of a pulse waveform according to a preferred embodiment of the present invention.

More particularly, in the preferred embodiment, the pulse waveform has a peak to average power ratio preferably greater than one and a repetition period preferably shorter than the afterglow duration of the luminescent substance. FIG. 5 shows a preferred waveform 500 with pulses 505 where power is supplied and periods 510 where no power is supplied. The waveform 500 has approximately a 3:1 peak-to-average ratio and a duty cycle of approximately 33%. The duty cycle for a particular embodiment preferably depends upon the characteristics of the phosphor used. In addition, alternative embodiments employ different duty cycles to control the wavelength of the output illumination. Additional embodiments include a duty cycle control, such as a switch or variable control, to vary the duty cycle during operation. The heat load is distributed between the beginning of one pulse and the beginning of the next pulse to produce an average heat load no greater than if the power were held at a constant (DC) level equal to the level of the pulse 505. The power supplied during a pulse 505 is preferably at a level approximately three times a sustainable DC level which would generate a heat load equal to the average heat load.

Figure 6:
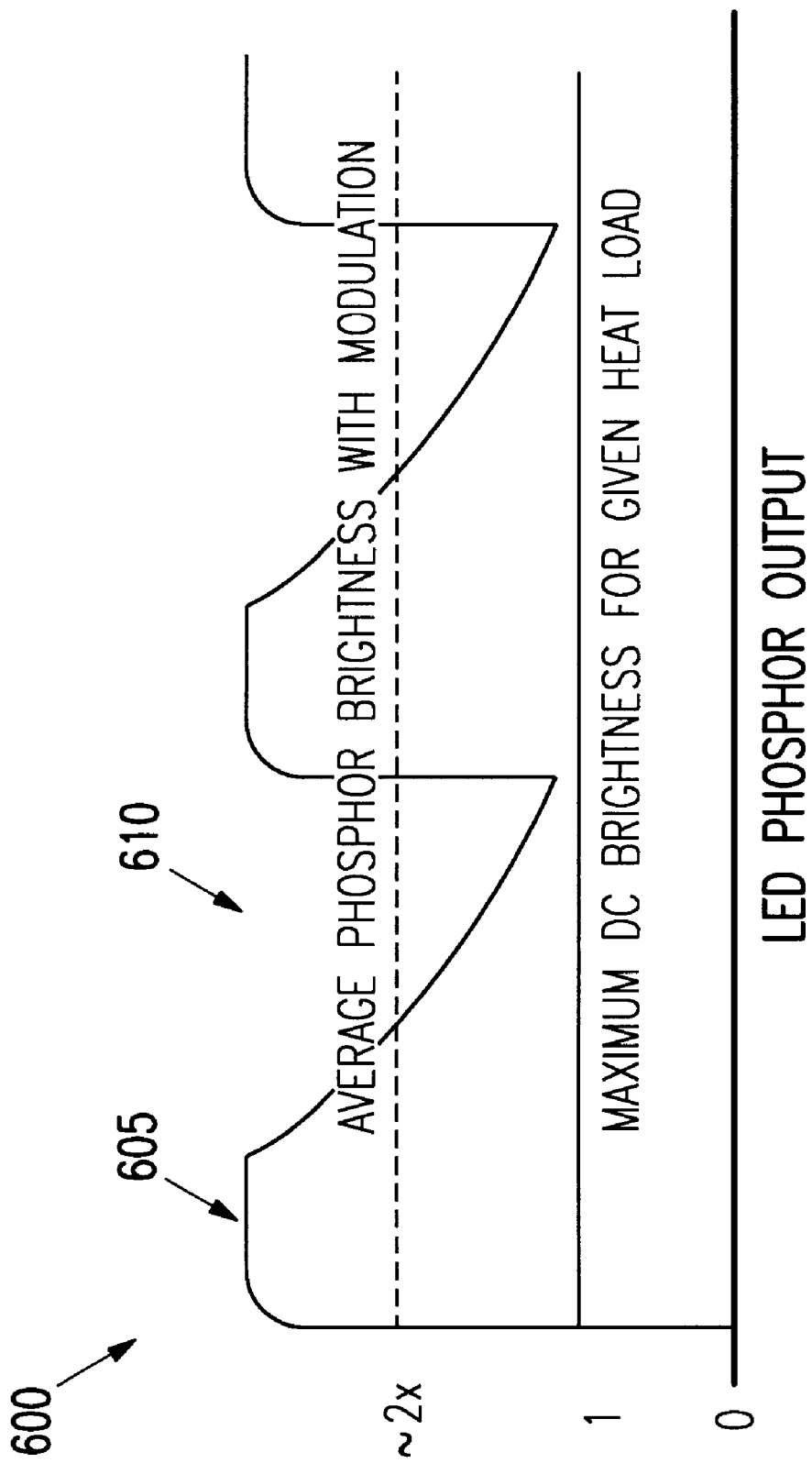
FIG. 6 is a chart of light emitted by an illumination device according to a preferred embodiment of the present invention.

FIG. 6 charts the light output 600 of a preferred embodiment including a short wavelength LED and phosphor. The average light output is preferably approximately twice that of an LED driven by direct current with a heat load equivalent to the average heat load produced by the preferred embodiment. During the time the LED drive waveform is on (i.e., the time when power is applied to the LED; pulse 505 in FIG. 5), the LED emits short wavelength light. Most of the light from the LED causes the phosphor system to phosphoresce at a characteristic white spectrum at a peak intensity 605. Thus, while the waveform is on, the LED and associated structures are heated by the power dissipation in the short wavelength LEDs. When the LED drive waveform is turned off (i.e., the time when power is not applied to the LED; period 510 in FIG. 5), the LED ceases to emit light and so no further power is dissipated in the LED. Thus, no more heat is added to the system. During this off-time, the phosphor continues to glow, but the intensity begins to decay exponentially with a characteristic time constant and so the light 610 emitted by the phosphor decays in the same manner.

The ratio of the discharge to charge times for the phosphor is preferably large enough that the phosphor is charged to near peak intensity level while the LED is on. When the LED is turned off, the phosphor continues to glow (i.e., afterglow). The emission decays approximately toward zero. Before the glow decay has progressed too far, the next pulse preferably again turns on the LED. The timing of the pulses is preferably controlled by the electronic control package 250 and the pulse generator 225 shown in FIG. 2. The light emitted from the LED pumps the phosphor, quickly returning the phosphor emission to peak level. The process is repeated to yield a continuous light output with high power efficiency.

An advantage of the preferred embodiment is that on average, two units of light are produced for one unit of heat relative to an LED powered by a DC source. One source of this efficiency is that, as shown in FIG. 2, for an equivalent heat load, 3 times the power is applied for ⅓ duty cycle compared to a direct current LED producing the same heat load. In addition, the phosphor continues to emit light, decaying all the while, during the LED off time (i.e., when no power is dissipated in the LED; period 510 in FIG. 5). Thus, the LED and associated structures tend to cool down during this interval (although the temperature change is very small, since the LED pulse modulation occurs on a time scale much shorter than the thermal time constant). The average power dissipated by the LED produces a proportional temperature rise. This rise and fall produces the average heat load. The brightness of the phosphor emissions is proportional to the average of the peak-and-decay waveform because the eye averages the phosphor emissions over a relatively long time constant. The time and duty cycle relationships between the LED emission, the peak and decay nature of the phosphors, the intensity time averaging of the eye and the thermal averaging of the heat load produced by the LED combine to provide advantages of the preferred embodiment.

Figure 7:
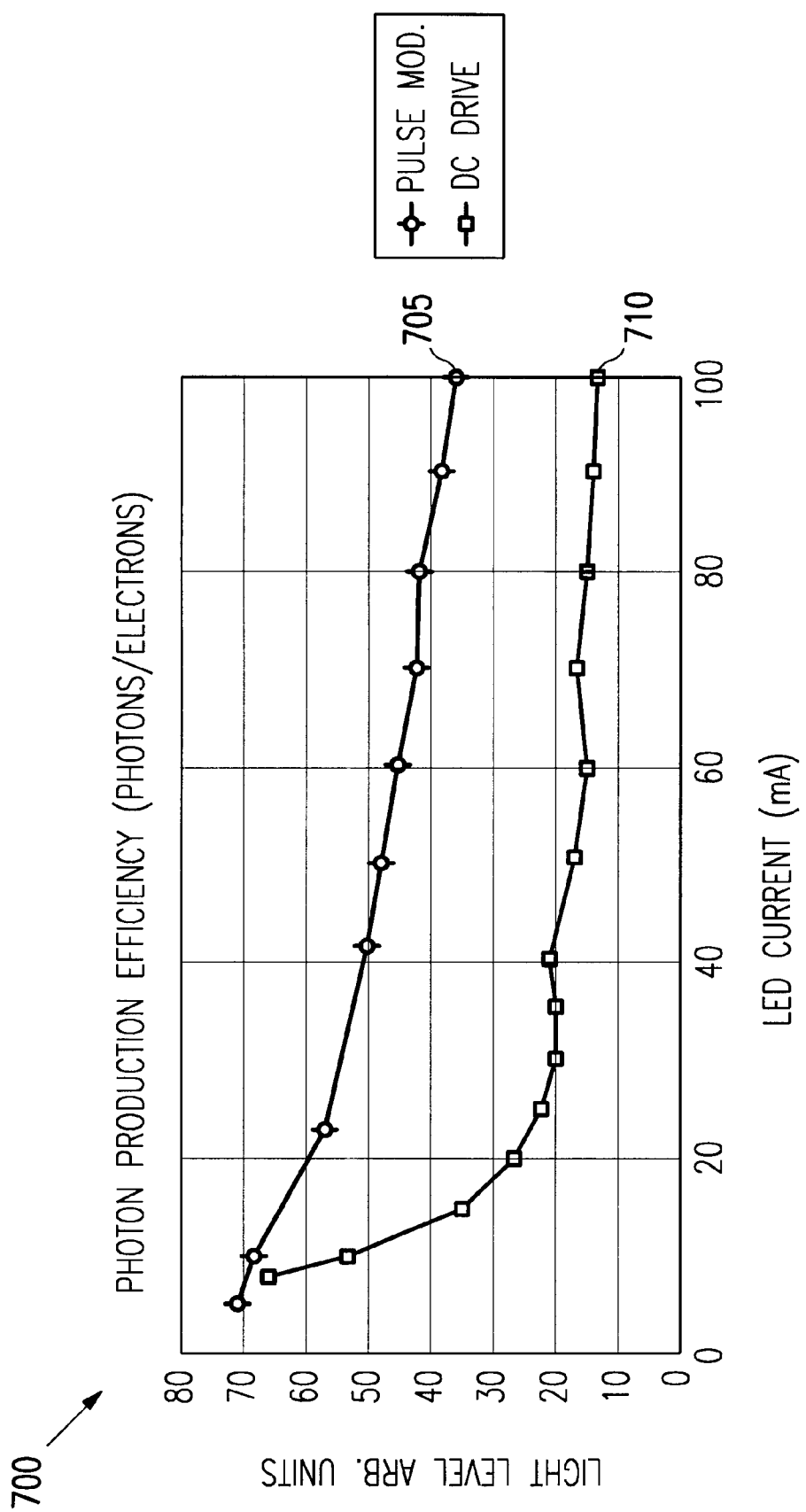
FIG. 7 is a chart of photon production efficiency of an illumination device according to a preferred embodiment of the present invention.

FIG. 7 shows a chart 700 of the efficiency of the preferred embodiment as compared to a direct current driven LED. Line 705 graphs (in arbitrary units) the photon production efficiency of the preferred embodiment for various LED currents. Line 710 graphs the photon production efficiency of a direct current driven LED. Lines 705 and 710 show that the preferred embodiment produces more photons per electron, especially at higher current levels. Thus, the preferred embodiment produces more output illumination for a given input current. One reason for this is the inability of the direct current driven LED to cool off, while the preferred embodiment takes advantage of a pulse waveform and a phosphor system to continue to emit light while the LED cools.

The optimum frequency of the pulse modulated power signal of FIG. 5 depends on the turn-on decay of the LEDs or other light source as well as the emission decay rate and the attack time (i.e., the time required for the phosphor to reach peak emission after illumination by the LED begins) of the phosphor system used in the illumination device. For standard phosphorescent LEDs, a pulse frequency of 30 kHz is preferred.

The preferred and alternative embodiments are useful anywhere bright cool illumination is desirable. One embodiment may be used as an improved light source for portable optical-based instruments, such as water turbidity monitors. Another may be combined into hand tools in order to illuminate an area of interest. Another may be used as a cool source of illumination for microscopes especially useful when illuminating sensitive specimens. Yet another application is to discretely illuminate the interior of handbags and purses.

A number of embodiments of the present invention have been described. Nevertheless, it will be understood that various modifications may be made without departing from the spirit and scope of the invention. For example, the exterior of the illumination device may be opaque or transparent. The pulse waveform may be of a variety of forms such as with a duty cycle of 10% or 50%. Accordingly, other embodiments are within the scope of the following claims.

What is claimed is:

1. An illumination device including:
   (a) a solid state light source for producing light;
   (b) a pulse modulation power control circuit for periodically activating the light source to produce light at a level above the light produced by a sustainable steady-state power level; and
   (c) a luminescent substance for producing illumination, where the luminescent substance produces illumination in response to light from the light source and further where the luminescent substance continues to produce illumination after the light source has stopped producing light;
   wherein the average light output of the light source is greater than the average light output obtainable from the light source at the sustainable steady-state power level.

2. The illumination device of claim 1 where the light source includes at least one light emitting diode.

3. The illumination device of claim 2 where at least one of the light emitting diodes is a short wavelength light emitting diode.

4. The illumination device of claim 1 further including a lens for focusing the illumination output by the illumination device.

5. The illumination device of claim 1 where the luminescent substance is a phosphor.

6. The illumination device of claim 1 where the luminescent substance emits white light.

7. The illumination device of claim 1 where the luminescent substance emits substantially no heat.

8. The illumination device of claim 1 where a duty cycle of the pulse modulation power control circuit is controlled by a duty cycle control.

9. The illumination device of claim 1 further including a power supply for supplying a power signal to the pulse modulation power control circuit.

10. An illumination device including:
    (a) at least one light emitting diode for producing light;
    (b) a power circuit for supplying a pulse modulated power signal to each light emitting diode to produce light at a level above the light produced by a sustainable steady-state power level;
    (c) a casing at least partially encompassing each light emitting diode and the power circuit; and
    (d) phosphor for producing illumination positioned in the illumination device such that the illumination is output by the illumination device, where the phosphor produces illumination in response to light from each light emitting diode and further where the phosphor continues to produce illumination after each light emitting diode has stopped producing light;
    wherein the average light output of the illumination device is greater than the average light output obtainable from the illumination device at the sustainable steady-state power level.

11. An illumination device including:
    (a) at least one light emitting diode for producing light;
    (b) phosphor for producing illumination positioned in the illumination device such that the illumination is output by the illumination device, where the phosphor produces illumination in response to light from each light emitting diode and further where the phosphor continues to produce illumination after each light emitting diode has stopped producing light;
    (c) a heat sink for dissipating heat produced by each light emitting diode;
    (d) a pulse generator for supplying a pulse modulated power signal to each light emitting diode to produce light at a level above the light produced by a sustainable steady-state power level, where the pulse generator produces the pulse modulated power signal by converting power received from a power supply; and
    (e) a casing at least partially encompassing each light emitting diode and the phosphor;
    wherein the average light output of the illumination device is greater than the average light output obtainable from the illumination device at the sustainable steady-state power level.

12. The illumination device of claim 11 further including a power supply for supplying a power signal to the pulse generator.

13. A method of producing illumination, the method including:
    (a) supplying a power signal to a light source, where the light source produces light in response to the power signal at a level above the light produced by a sustainable steady-state power level and causes a luminescent substance to produce illumination;
    (b) ceasing to supply a power signal to the light source, where the light source ceases to produce light in response to the ceasing of the power signal, and where the luminescent substance produces a gradually decaying illumination after the light source ceases to produce light; and
    (c) repeating steps (a) and (b) to produce an average illumination;
    wherein the average light output from the light source is greater than the average light output obtainable from the light source at the sustainable steady-state power level.

14. The method of claim 13 where the light source includes at least one light emitting diode.

15. A method of producing an output illumination, the method including:
    (a) supplying a power signal to at least one light emitting diode, where each light emitting diode produces light in response to the power signal at a level above the light produced by a sustainable steady-state power level and causes a phosphorescent substance to produce illumination;

(b) ceasing to supply a power signal to said at least one light emitting diode, where each light emitting diode ceases to produce light in response to the ceasing of the power signal to such light emitting diode; and (c) repeating steps (a) and (b) to produce the output illumination;

wherein the average light output of the at least one light emitting diode is greater than the average light output obtainable from the at least one light emitting diode at the sustainable steady-state power level.

16. A system for producing illumination, the system including:

(a) means for supplying a power signal to a light source, where the light source produces light in response to the power signal at a level above the light produced by a sustainable steady-state power level and causes a luminescent substance to produce illumination;

(b) means for ceasing to supply a power signal to the light source, where the light source ceases to produce light in response to the ceasing of the power signal, and where the luminescent substance produces a gradually decaying illumination after the light source ceases to produce light; and (c) means for repeating steps (a) and (b) to produce an average illumination;

wherein the average light output of the light source is greater than the average light output obtainable from the light source at the sustainable steady-state power level.

17. The system of claim 16 where the light source includes at least one light emitting diode.

18. A system for producing an output illumination, the system including:

(a) means for supplying a power signal to at least one light emitting diode, where each light emitting diode produces light in response to the power signal at a level above the light produced by a sustainable steady-state power level and causes a phosphorescent substance to produce illumination;

(b) means for ceasing to supply a power signal to said at least one light emitting diode, where each light emitting diode ceases to produce light in response to the ceasing of the power signal to such light emitting diode; and (c) means for repeating steps (a) and (b) to produce the output illumination;

wherein the average light output of the at least one light emitting diode is greater than the average light output obtainable from the at least one light emitting diode at the sustainable steady-state power level.

* * * * *